United States Patent [19]

Bell

[11] 4,049,715

[45] Sept. 20, 1977

[54] 3-[2-(4-ANISIDINO)PHENYL]-1-PHENYL-1-PROPIOPHENONES AND PROPANOLS

[75] Inventor: Malcolm R. Bell, East Greenbush, N.Y.

[73] Assignee: Sterling Drug Inc., New York, N.Y.

[21] Appl. No.: 593,166

[22] Filed: July 3, 1975

Related U.S. Application Data

[60] Continuation-in-part of Ser. No. 402,162, Oct. 1, 1973, Pat. No. 3,994,902, which is a division of Ser. No. 156,070, June 23, 1971, Pat. No. 3,819,637.

[51] Int. Cl.$^2$ .............................................. C07C 93/14
[52] U.S. Cl. ....................................... 260/571; 544/63; 544/106; 560/9; 560/19; 536/31; 260/268 BQ; 260/268 PH; 260/283 SY; 260/286 R; 260/287 R; 260/289 R; 260/562 A; 260/562 B; 260/566 D; 260/566 F; 260/570.5 R; 260/570.7; 424/258
[58] Field of Search ........................ 260/570.5 R, 571

[56] References Cited

PUBLICATIONS

Bell et al., "Journal of Medicinal Chemistry", vol. 13, No. 4, pp. 664–668, (1970).

Primary Examiner—Robert V. Hines
Attorney, Agent, or Firm—Frederik W. Stonner; B. Woodrow Wyatt

[57] ABSTRACT

The invention relates to novel 1-(4-$R_1$O-phenyl)-2-(4-$R_2$-phenyl)-6-$R_3$-1,2,3,4-tetrahydroquinolines having anti-fertility and hypocholesterolemic activities, to their preparation, and to novel intermediates therefor.

7 Claims, No Drawings

3-[2-(4-ANISIDINO)PHENYL]-1-PHENYL-1-PROPIOPHENONES AND PROPANOLS

This application, of which application Ser. No. 686,074, filed May 13, 1976, is a division, is a continuation-in-part of copending application Ser. No. 402,162, filed Oct. 1, 1973, now U.S. Pat. No. 3,994,902, issued Nov. 30, 1976, which in turn is a division of prior application Ser. No. 156,070, filed June 23, 1971, now U.S. Pat. No. 3,819,637, issued June 25, 1974.

The invention relates to novel derivatives of 1,2-diphenyl-1,2,3,4-tetrahydroquinolines (formula I below), to their preparation, and to novel intermediates for their preparation.

According to one aspect of the invention there is provided novel 1-(4-$R_1$O-phenyl)-2-(4-$R_2$-phenyl)-6-$R_3$-1,2,3,4-tetrahydroquinolines of the formula

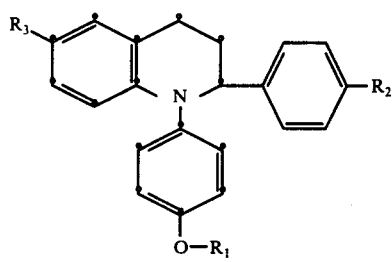

I where $R_1$ is hydrogen, lower-alkyl, benzyl, or $C_nH_{2n}NR_4R_5$, where $R_4$ and $R_5$, which can be the same or different, are lower-alkyl or $R_4$ and $R_5$ together with nitrogen form a heterocyclic ring selected from 1-pyrrolidyl, 1-piperidyl, 1-piperazinyl, 4-lower-alkyl-1-piperzinyl, 4-phenyl-1-piperazinyl, 4-morpholinyl, 4-thiomorpholinyl and such rings substituted on carbon by from one to three lower-alkyl substituents and $n$ is an integer from 2 to 4 inclusive; and $R_2$ and $R_3$, which can be the same or different, are hydrogen, lower-alkyl, lower-alkoxy, or halo.

A preferred group of compounds of the invention having formula I above are those wherein $R_1$ is $C_nH_{2n}NR_4R_5$. A particularly preferred group of compounds are those wherein $R_1$ is $C_nH_{2n}NR_4R_5$ where $n$ is the integer 2.

According to another aspect of the invention there is provided novel N,1,3-triphenylpropylamines of the formula

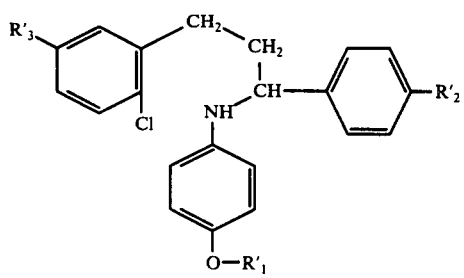

II where $R'_1$ is lower-alkyl or benzyl; $R'_2$ is hydrogen, lower-alkoxy or halo; and $R'_3$ is hydrogen or lower-alkoxy.

According to yet another aspect of the invention there is provided a novel diphenylpropanol to phenylpropiophenone of the formula

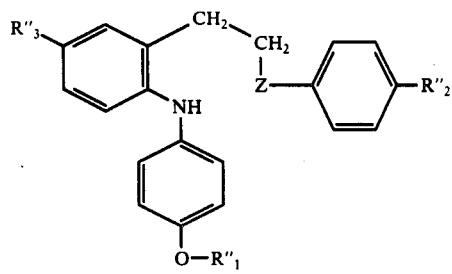

III where $R''_1$ is lower-alkyl, benzyl, or $C_nH_{2n}NR_4R_5$ $n$ where $R_4$, $R_5$ and $n$ have the meaning defined for $R_4$, $R_5$ and $n$ of formula I; $R''_2$ is hydrogen, lower-alkoxy or halo; $R''_3$ is hydrogen or lower-alkoxy; and Z is carbonyl (C=O) or hydroxymethylene (CHOH).

According to a further aspect of this invention there is provided a novel 1-phenyl-3,4-dihydrocarbostyril of the formula

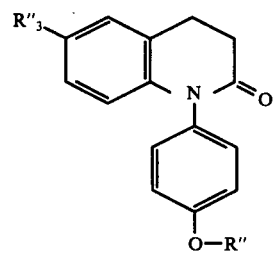

IIIA where $R''$ is hydrogen, lower-alkyl, benzyl or $C_nH_{2n}NR_4R_5$, where $R_4$, $R_5$ and $n$ have the meaning defined for $R_4$, $R_5$ and $n$ of formula I; and $R''_3$ is hydrogen or lower-alkoxy.

According to still another aspect of the invention there is provided a novel 1,2-diphenylquinolone of the formula

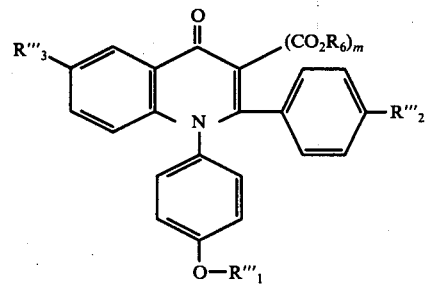

IV where $R'''_1$ is hydrogen, lower-alkyl, benzyl or $C_nH_{2n}NR_4R_5$, where $R_4$, $R_5$ and $n$ have the meaning defined hereinabove for $R_4$, $R_5$ and $n$ of formula I; $R'''_2$ and $R'''_3$, which can be the same or different, are hydrogen, lower-alkyl, lower-alkoxy or halo; $R_6$ is hydrogen or lower-alkyl; and $m$ is an integer from 0 to 1 inclusive.

The novel compounds having formula II, formula III, formula IIIA and formula IV are useful as intermediates in the preparation of the novel 1-(4-$R_1$O-phenyl)-2-(4-$R_2$-phenyl)-6-$R_3$-1,2,3,4-tetrahydroquinolines of formula I.

Throughout this specification the terms "lower-alkyl" and "lower-alkoxy" each mean a group preferably having from one to six carbon atoms which can be arranged in a straight or branched chain as illustrated, without limiting the generality of the foregoing, by methyl, ethyl, propyl, isopropyl, butyl, sec.-butyl, pentyl and hexyl for lower-alkyl and methoxy, ethoxy, propoxy, isopropoxy, butoxy and hexyloxy for lower-alkoxy.

Throughout this specification the designation $C_nH_{2n}$, where $n$ is an integer from 2 to 4, represents straight or branched alkylene as illustrated by $-CH_2CH_2-$, $-CH_2CH_2CH_2-$, $-CH_2CH(CH_3)-$, $-CH_2CH_2CH_2CH_2-$, $-CH(CH_3)-CH(CH_3)-$.

Throughout this specification where $C_nH_{2n}NR_4R_5$ comprehends heterocyclic rings substituted on carbon by from one to three lower-alkyl substituents, the lower-alkyl substituents can be attached to any available ring carbon atom, and such rings are illustrated by, but not limited to, 2-methyl-1-piperidyl, 4-methyl-1-piperidyl, 3-ethyl-1-piperidyl, 2,6-dimethyl-1-piperidyl, 2,4-dimethyl-1-piperidyl, 2,4,6-trimethyl-1-piperidyl, 3-propyl-1-piperidyl, 2,5-dimethyl-1-pyrrolidyl, 2,3-dimethyl-4-morpholinyl, 2-ethyl-4-morpholinyl, 3-ethyl-1-piperazinyl and 2,4,6-trimethylpiperazinyl.

Throughout this specification the term halo means bromo, chloro, fluoro and iodo.

In the process aspects of the invention, the compounds of formula I are prepared by several methods, designated herein as Methods A, B, C, D and E, more fully described hereinbelow.

Method A provides compounds of formula I where $R_1$ represents $C_nH_{2n}NR_4R_5$, hereinabove defined, lower-alkyl, or benzyl and involves alkylation of the corresponding compound where $R_1$ is hydrogen with an appropriate amino-lower-alkyl halide or lower-alkyl halide, i.e., $Y-C_nH_{2n}NR_4R_5$ or lower-alkyl-Y, where Y is chlorine, bromine or iodine, or benzyl chloride respectively.

Method B provides compounds of formula I where $R_1$ is hydrogen and involves demethylation or debenzylation of the corresponding compounds where $R_1$ is methyl or benzyl respectively.

Method C provides certain compounds of formula I where $R_1$ is lower-alkyl and involves cyclization of the corresponding N,1,3-triphenylpropylamines of formula II above.

Method D provides certain compounds of formula I where $R_1$ is lower-alkyl, benzyl or $C_NH_{2n}NR_4R_5$, as hereinabove defined, and involves cyclization of the corresponding diphenylpropanols or phenylpropiophenones of formula III.

Method E provides compounds of formula I where $R_1$ is hydrogen, lower-alkyl or $C_nH_{2n}NR_4R_5$, as defined hereinabove, and involves reduction of 1,2-diphenyl-quinolones of formula IV where $m$ is the integer 0. When compounds of formula IV where $R'''_1$ is benzyl are reduced, the benzyl moiety is concurrently reductively cleaved giving the corresponding compound of formula I where $R_1$ is hydrogen.

The alkylation process of Method A is carried out using standard procedures, i.e., by converting I ($R_1$=H) to a corresponding suitable alkali metal salt which is then reacted with the appropriate amino-lower-alkyl halide, i.e., $Y-C_nH_{2n}NR_4R_5$, lower-alkyl halide or benzyl chloride in a suitable inert solvent to give the corresponding compound where $R_1=C_nH_{2n}NR_4R_5$, lower-alkyl or benzyl respectively. The reaction is conveniently performed by treating I ($R_1$=H) with about an equivalent of sodium methoxide in a suitable solvent, e.g., chlorobenzene at about 100° C. with concurrent distillation of the methyl alcohol so formed, and treatment of the resulting sodium salt (I,$R_1$=Na) with about an equivalent of the appropriate amino-lower-alkyl halide, lower-alkyl halide or benzyl chloride. The amino-lower-alkyl halides and lower-alkyl halides belong to a well-known class of compounds which are readily available commercially or preparable by standard procedures.

The demethylation process of Method B is carried out using either one of two standard procedures, i.e., by treating I ($R_1=CH_3$) with hydrogen bromide in aqueous acetic acid or alternatively, with potassium hydroxide in a suitable solvent. In the first procedure the reaction is conveniently performed by heating a solution of I ($R_1=CH_3$) in glacial acetic acid with an excess of hydrogen bromide in a nitrogen atmosphere at reflux for about three hours; in the alternative procedure the reaction is conveniently performed by heating I ($R_1=CH_3$) with about an equal weight of potassium hydroxide in diethylene glycol for about eight hours at about 220° C.

The debenzylation process of Method B is carried out using a standard catalytic hydrogenolysis procedure. The reaction can be conveniently performed by subjecting a solution of I ($R_1$=benzyl) in ethyl alcohol, in the presence of about ten percent by weight of I of palladium on charcoal catalyst (10%), to a hydrogen atmosphere at about atmospheric pressure until the stoichiometric amount of hydrogen has reacted.

The cyclization process of Method C is carried out by treating II with potassium amide in liquid ammonia. The reaction is conveniently performed by adding II to an excess of potassium amide in liquid ammonia in a dry atmosphere and stirring the mixture while the liquid ammonia is allowed to evaporate.

The cyclization process of Method D is carried out by either of two procedures. In a preferred procedure, the reaction is performed by heating diphenylpropanol III (Z is CHOH) in a suitable solvent in the presence of an acid catalyst. The reaction is conveniently performed by heating a solution of the diphenylpropanol in xylene in the presence of p-toluene sulfonic acid (about ten percent by weight of the diphenylpropanol) at reflux for about three hours. The diphenylpropanol is obtained from the phenylpropiophenone III (Z is C=O) by catalytic hydrogenation as described below or, preferably, by standard hydride reduction. A convenient procedure is treatment of the phenylpropiophenone in ethyl alcohol with excess sodium borohydride at room temperature for about three hours or, alternatively, in tetrahydrofuran with excess lithium aluminum hydride at reflux temperature for about fourteen hours. In an alternative procedure the cyclization process is carried out by catalytic hydrogenation of the phenylpropiophenone III (Z is C=O) which yields the corresponding compound I directly together with the corresponding diphenylpropanol III (Z is CHOH) in about a ratio of 45 to 55 respectively; the diphenylpropanol is cyclized to the corresponding compound I as described above. The catalytic hydrogenation is conveniently performed by subjecting a solution of the phenylpropiophenone in ethyl alcohol to a hydrogen atmosphere over ten percent palladium on charcoal (about thirty percent by weight of the phenylpropiophenone) at about 60° C. and about 35 pounds per square inch gauge until the stoichiometric amount of hydrogen has reacted. The resulting mixture of cyclized product and diphenylpropanol is separated by standard chromatographic procedures.

The reductive process of Method E is carried out by treating the 1,2-diphenylquinolone IV in a suitable solvent with lithium aluminum hydride and aluminum chloride. The reaction is conveniently performed by heating a solution of IV in dry tetrahydrofuran with an excess of a lithium aluminum hydride - aluminum chloride mixture (8 to 1 mole ratio) at reflux for about sixteen hours.

The novel N,1,3-triphenylpropylamines of formula II are prepared by condensing an appropriate 2-chloro or 2-bromobenzaldehyde with an appropriate acetophenone, hydrogenating the resulting chalcone, condensing the propanone so obtained with an appropriate aniline, and chemically reducing the resulting imine. The sequence of reactions is illustrated in the following equations:

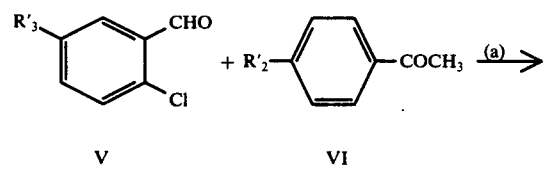

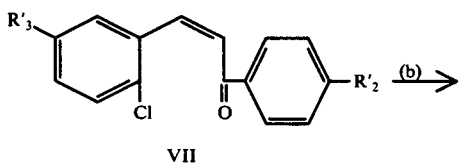

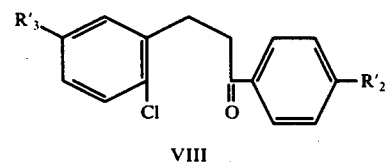

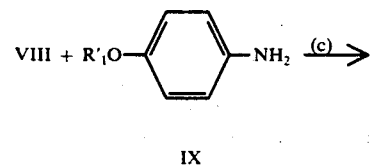

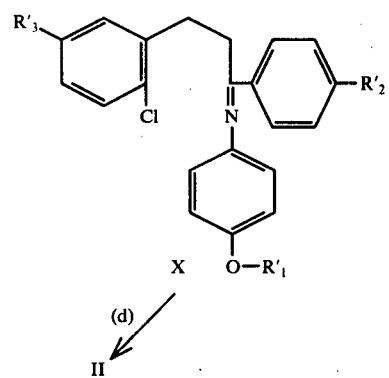

The condensation step (a) is carried out by treating the aldehyde V with the acetophenone VI in ethyl alcohol in the presence of aqueous sodium hyrdroxide at room temperature for about one hour. The aldehydes (V) and acetophenones (VI) belong to classes of known compounds and can be prepared by standard procedures. The hydrogenation step (b) is carried out by subjecting a solution of chalcone VII in ethyl alcohol to a hydrogen atmosphere in the presence of Raney nickel at elevated pressure and room temperature. An initial pressure of about 165 pounds per square inch gauge is satisfactory. The condensation step (c) is carried out by reacting the propanone VIII with the aniline IX in a suitable solvent, e.g., xylene, in the presence of a catalytic amount of zinc chloride at reflux temperatures with concurrent azeotropic removal of the water so formed until the stoichiometric quantity of water is collected. The anilines (IX) belong to a class of known compounds and are readily available commercially or preparable by standard procedures. The reduction step (d) is carried out by heating a solution of the imine X in dry tetrahydrofuran in the presence of excess lithium aluminum hydride for about two hours.

The novel phenylpropiophenones of formula III (Z is C=O) are prepared by reacting an appropriate 1-phenyl-3,4-dihydrocarbostyril with an appropriate phenyllithium. The appropriate 1-phenyl-3,4-dihydrocarbostyril (XV A below) is obtained by acylating an appropriate aniline with the known 3-chloropropionyl chloride, cyclizing the resulting anisidide, and reacting the dihydrocarbostyril obtained with an appropriate phenyl bromide; alternatively the appropriate 1-phenyl-3,4-dihydrocarbostyril where $R_7$ is lower-alkyl (XV below) is obtained by reacting an appropriate 2-chloroquinoline with the sodium salt of an appropriate phenol, thermal rearrangement of the resulting 2-phenoxyquinoline and reduction of the 1-phenylcarbostyril so obtained. This sequence of reactions is illustrated in the following equations:

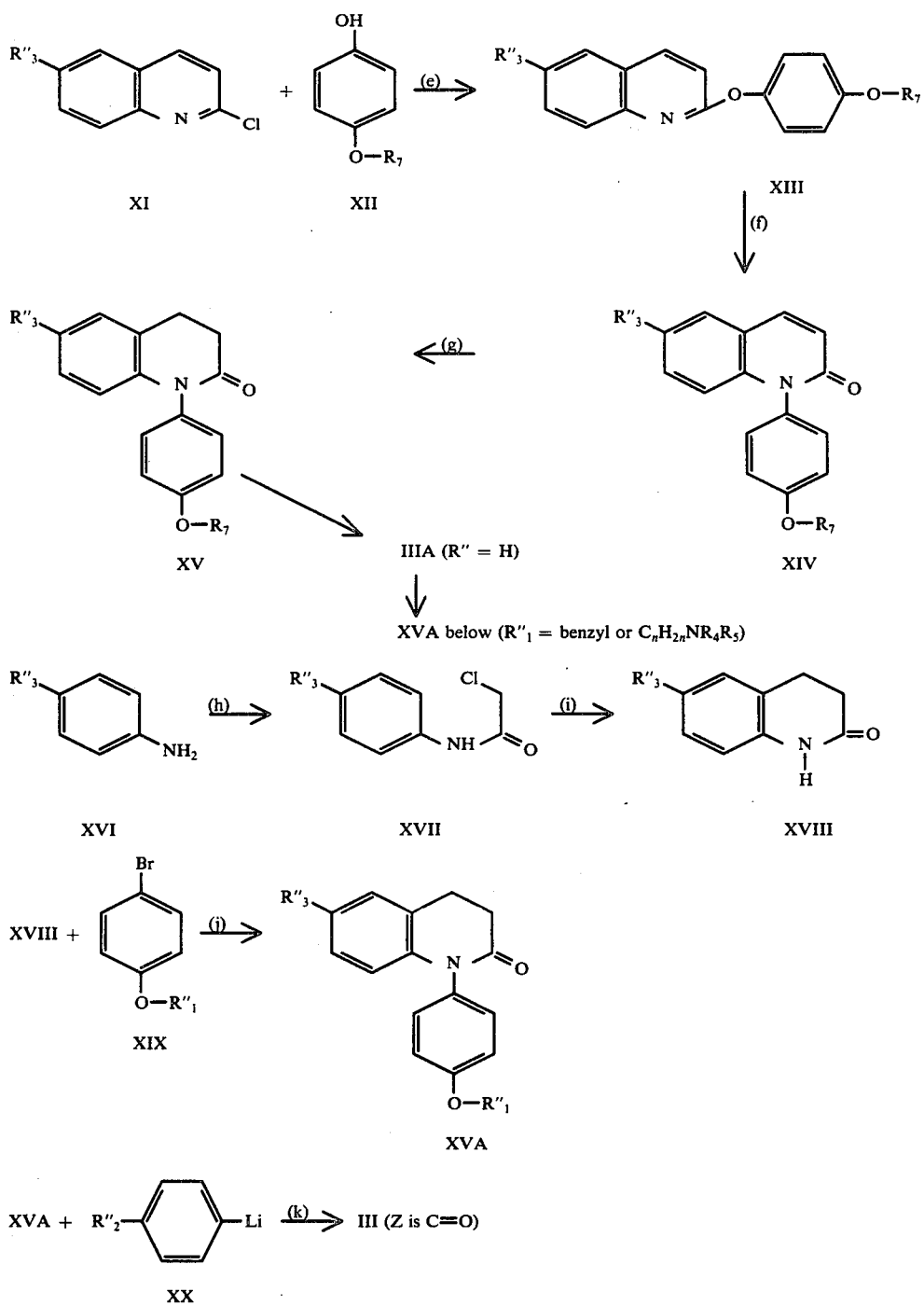

Step (e) is carried out by heating the 2-chloroquinoline XI with the sodium salt of the phenol XII, where $R_7$ is lower-alkyl, in a suitable solvent. The reaction is readily performed in a solvent mixture of dimethylformamide and 1,2-dimethoxyethane at reflux temperature for about sixteen hours. The 2-chloroquinolines (XI) and phenols (XII) belong to known classes of compounds and can be prepared by standard procedures. The rearrangement step (f) is carried out by heating the 2-phenoxyquinoline XIII in extra heavy mineral oil in a nitrogen atmosphere at reflux for about four hours. The reduction step (g) is carried out by subjecting the 1-phenylcarbostyril (XIV) to a hydrogen atmosphere over Raney nickel until the stoichiometric quantity of hydrogen has reacted. The reaction is readily performed in ethyl alcohol at a temperature of about 50°-60° C. and at a pressure of about 550 pounds per square inch gauge. The acylation step (h) is carried out by reacting the aniline XVI with 3-chloropropionyl chloride in acetone at reflux temperature for about one hour. The anilines (XVI) belong to a known class of compounds and can be prepared by standard procedures. The cyclization step (i) is carried out by heating the anisidide XVII with excess aluminum chloride at about 150° C. for about one-half hour. In the case where the anisidide bears a methoxyl substituent ($R''_3$ = $OCH_3$), the corresponding hydroxy carbostyril is obtained (XVIII, R″₃ = OH) which is converted to the corresponding methoxy carbostyril (R″₃ = OCH₃) on treatment with dimethyl sulfate in the presence of aqueous sodium hydroxide. Step (j) is carried out by heating a mixture of the carbostyril XVIII, the phenyl bromide XIX, potassium carbonate and copper powder at about 250° to 255° C. for about eighteen hours. The phenyl bromide XIX is prepared from the sodium salt of the known 4-bromophenol by standard alkylation procedures, similar to those described hereinbefore for Method A, using the appropriate lower-alkyl halide or amino-lower-alkyl halide. Step (k) is carried out by reacting the 1-phenyl-3,4-dihydrocarbostyril XVA, obtained by either of the above disclosed procedures, with an excess of the phenyllithium XX in a suitable solvent under nitrogen at elevated temperatures. The reaction is readily performed in benzene at reflux temperature for about three hours. The phenyllithiums (XX) belong to a class of known compounds or are readily prepared by standard procedures from the corresponding phenyl bromide by reaction with butyllithium in a nitrogen atmosphere in an inert solvent, such as ether, at room temperature. The 1-phenyl-3,4-dihydrocarbostyril XVA, where R″₁ is benzyl or C$_n$H$_{2n}$NR$_4$R$_5$ are also obtained from the 1-phenyl-3,4-dihydrocarbostyril IIIA, where R″ is hydrogen, by benzylation with benzyl chloride or alkylation with amino-lower-alkyl halide (Y-C$_n$H$_{2n}$NR$_4$R$_5$) using a procedure similar to that described in Method A. The 1-phenyl-3,4-dihydrocarbostyril IIIA, where R″ is hydrogen, is obtained from the corresponding 1-phenyl-3,4-dihydrocarbostyril XV where R₇ is methyl using the demethylation procedures described in Method B.

The novel 1,2-diphenylquinolones of formula IV, where m is the integer 0, are prepared by three methods. In a first method the 1,2-diphenylquinolones (IV, m=0) are prepared by reaction of an appropriate N-phenylisatoic anhydride with an appropriate lower-alkyl benzoylacetate, hydrolysis of the resulting 1,2-phenylquinolone-3-carboxylate to the corresponding 3-carboxy compound and pyrolytic elimination of the carboxyl group. In a second method the 1,2-diphenylquinolones (IV, m=0) are prepared by reaction of an appropriate N-phenylisatoic anhydride with sodium methylsulfinylmethide (hereinafter dimsyl sodium), and reaction of the methylsulfinylacetophenone so obtained with an appropriate benzaldehyde. The N-phenylisatoic anhydride is prepared by reacting an appropriate 2-bromo (or chloro)benzoic acid with an appropriate aniline and reacting the resulting anthranilic acid with ethyl chloroformate. These steps are illustrated by the following equations:

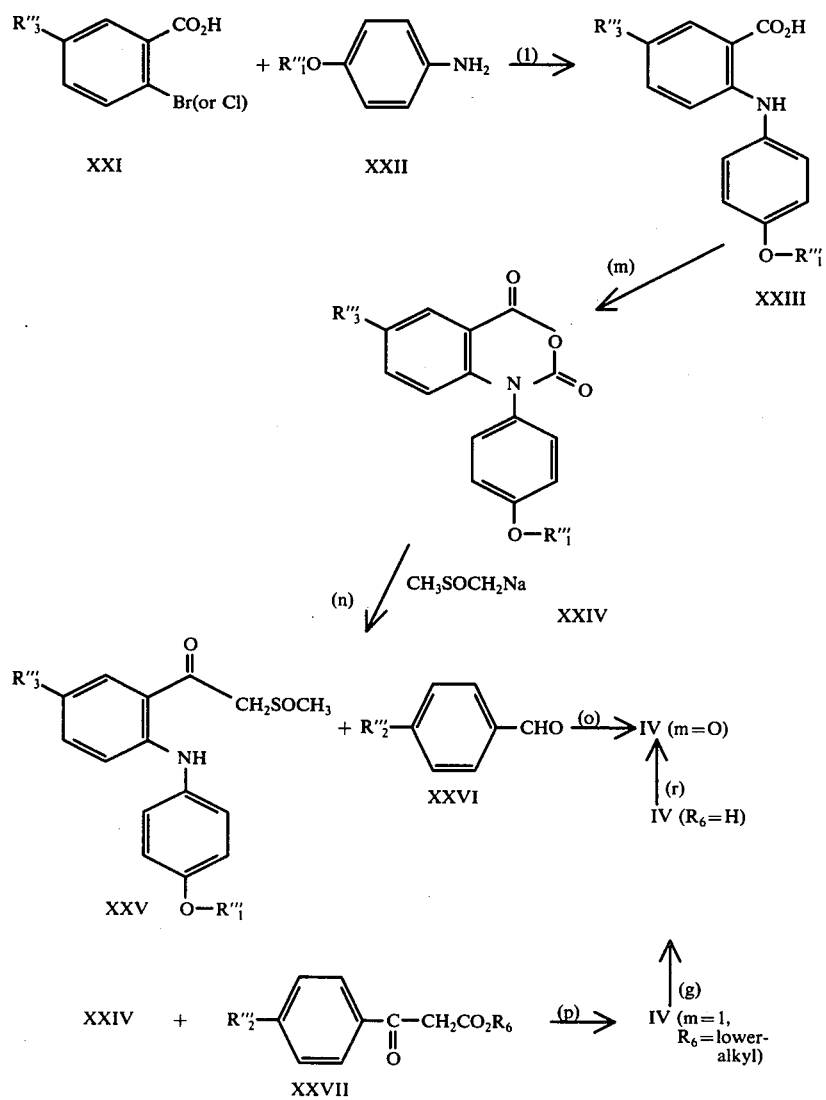

Step (1) is carried out by reacting the 2-bromo (or chloro)benzoic acid XXI with the aniline XXII in a suitable solvent in the presence of potassium carbonate and activated copper powder at elevated temperatures. The reaction is readily performed in amyl alcohol at reflux temperature for about four hours. The 2-bromo(or chloro)benzoic acids (XXI) are known or are readily prepared by standard procedures by treating an In a third method the 1,2-diphenylquinolones (IV, $m = 0$) are prepared by acylation of an appropriate aniline with an appropriate benzoyl chloride, chlorination of the resulting benzanilide, reaction of the benzimidoyl chloride so obtained with an appropriate 2-hydroxyacetophenone and rearrangement of the resulting 2-acetylphenyl N-phenylbenzimidate. The sequence of reactions is illustrated by the following equations:

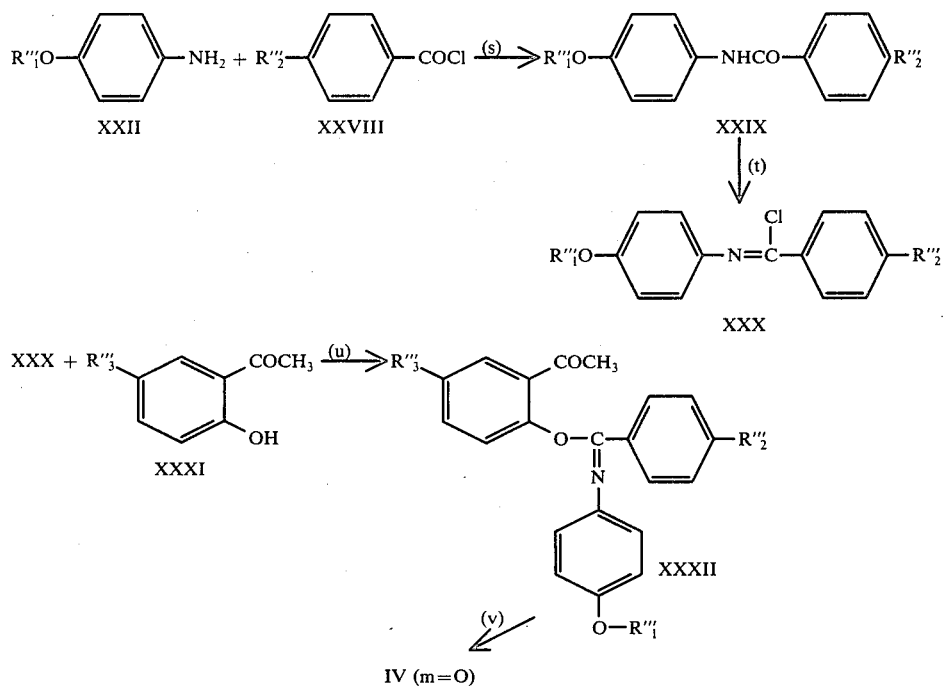

appropriate benzoic acid in acetic acid with bromine and water at elevated temperatures. The anilines (XXII) belong to a class of known compounds and can be prepared by standard procedures. The step (m) is accomplished by heating the anthranilic acid XXIII with ethylchloroformate at reflux temperature for about fifteen hours. Step (n) is accomplished by reacting the N-phenylisatoic anhydride XXIV with excess dimsyl sodium in dimethylsulfoxide in a nitrogen atmosphere. The reaction is readily carried out initially at room temperature followed by heating to about 50° C. for about one hour. Step (o) is accomplished by reacting the methylsulfinylacetophenone XXV with an equivalent of the benzaldehyde XXVI in benzene containing a trace of pyridine at reflux temperature for about three hours. The benzaldehydes (XXVI) belong to a class of known compounds and are prepared by standard procedures. Step (p) is accomplished by reacting the N-phenylisatoic anhydride XXIV with the lower-alkyl benzoylacetate XXVII in dimethyl sulfoxide in a nitrogen atmosphere in the presence of dimsyl sodium at about 50° C. until gas evolution ceases and continuing heating at about 70° C. for about an hour. The lower-alkyl benzoylacetates (XXVII) belong to a class of known compounds and are prepared by standard procedures. Hydrolysis step (g) is accomplished using standard procedures, e.g., by heating the 1,2-diphenylquinolone-3-carboxylate IV ($m = 1$, $R_6$ = lower-alkyl) with excess sodium hydroxide in aqueous ethyl alcohol for about one-half to one hour. Step (r) is accomplished by heating the 1,2-diphenyl-3-carboxylic acid IV ($m = 1$, $R_6 = H$) at about 280° C. until gas evolution ceases.

Step (s) is accomplished by reacting the aniline XXII with the benzoyl chloride XXVIII in ethylene dichloride in the presence of triethylamine in a temperature range of about 10° to 20° C. The benzoyl chlorides (XXVIII) belong to a class of known compounds and are prepared by standard procedures for the corresponding known benzoic acids, e.g., reaction with thionyl chloride. Step (t) is accomplished by reacting the benzanilide XXIX with phosphorus pentachloride at reflux temperature for about two hours. Step (u) is accomplished by treating the benzimidoyl chloride XXX in ethyl acetate with an excess of the 2-hydroxyacetophenone XXXI and an equivalent (based on XXXI) of sodium methoxide in dry methyl alcohol at room temperature for about fifteen hours. The 2-hydroxyacetophenones (XXXI) belong to a class of known compounds and are prepared by standard procedures. Step (v) is accomplished by heating the 2-acetylphenyl-N-phenylbenzimidate XXXII in a nitrogen atmosphere to about 250° C., removing external heating until the heat of the exothermic reaction subsides and continuing heating at about 250° C. for about one-half hour.

The 1,2-diphenylquinolones (IV, $m = 0$, $R'''_1 = C_nH_{2n}NR_4R_5$) are obtained from the corresponding 1,2-diphenylquinolones where $R'''_1$ is hydrogen by the standard alkylation procedure described hereinabove for Method A using the appropriate amino-alkyl-halide. The 1,2-diphenylquinolones (IV, $m = 0$, $R'''_1 = H$) are obtained from the corresponding 1,2-diphenylquinolones where $R'''_1$ is methyl or benzyl by the demethylation or debenzylation procedures described hereinabove for Method B.

In the foregoing described processes, the designations $R_{1-6}$, $R'_{1-3}$, $R''$, $R''_{1,3}$, $R'''_{1-3}$, Z and n have the meanings defined hereinbefore for these designations in formulas I, II, III, IIIA and IV, except where otherwise indicated.

The compounds as illustrated by the compounds of formula I, where $R_1$ is $C_nH_{2n}NR_4R_5$, are useful both in the free base form and in the form of acid-addition salts, and both forms are within the purview of the invention. The acid-addition salts are simply a more convenient form for use, and in practice, use of the salt form inherently amounts to use of the base form. For pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts, so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydriodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzene-sulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzene-sulfonate, p-toluenesulfonate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

Although medicinally acceptable salts of said basic compounds are preferred for pharmaceutical purposes, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The compounds of formula I of this invention possess useful pharmacological properties. Thus they possess useful antifertility and hypocholesterolemic activities as determined by standard test procedures, described hereinbelow. The actual determination of the numerical biological data definitive for a particular compound, for each type of activity, is readily determined by standard test procedures by technicians having ordinary skill in pharmacological test procedures, without the need for any extensive experimentation.

The compounds can be prepared for use by dissolving under sterile conditions salt forms of the compounds in water (or an equivalent amount of a non-toxic acid if the free base is used), or in a physiologically compatable aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Still further the compounds can be formulated for oral administration in aqueous alcohol, propylene, glycol, or oil solutions or oil-water emulsions in the same manner as conventional medicinal substances are prepared.

TEST PROCEDURE FOR THE DETERMINATION OF ANTIFERTILITY ACTIVITY

Mature female rats were medicated daily with the test agent for six days after insemination by proven male rats (a total of six medications). The rats were autopsied fifteen days after insemination and their uteri were removed and examined for evidence of pregnancy. The test agents were administered either as suspensions, depending on solubility and dosage level, in ten percent ethyl alcohol — cottonseed oil.

The compounds of formula I of this invention were found to be effective as antifertility agents, completely preventing pregnancy when administered either subcutaneously or orally to female rats in the dosage range of from 50 to 100 mg./kg. × 6 days (calculated on the basis of the free base) according to the procedure described above. Thus they are indicated for use as antifertility agents.

TEST PROCEDURE FOR THE DETERMINATION OF HYPOCHOLESTEROLEMIC ACTIVITY

Male rats were fasted for five hours, medicated with the test agent in gum tragacanth via stomach tube and then fed. This regimen was continued four days. A control group of male rats was subjected to the same regimen except that they were not medicated with the test agent. On the fifth day, blood was taken by cardiac puncture and serum samples were analyzed for cholesterol. The test agents were considered to have hypocholesterolemic activity if there was a significant decrease ($>15\%$) in the serum cholesterol level of the medicated rats from that of the control rats.

The compounds of formula I were found to effectively decrease serum cholesterol levels by from 43 to 80% when administered by gavage to male rats in the dose range of 4 to 128 mg./kg. × 4 days according to the above test procedure. Thus they are indicated for use as hypocholesterolemic agents, that is, as agents for lowering blood cholesterol levels.

The molecular structures of the compounds of this invention were assigned on the basis of the method of their synthesis and study of their infrared spectra, and confirmed by the correspondence between calculated and found values for the elementary analysis for representative examples.

The following examples will further illustrate the invention:

EXAMPLE 1

1-{4-[2-(Diethylamino)ethoxy]phenyl}-2-phenyl-1,2,3,4-tetrahydroquinoline.

A mixture of 15 g. 1-(4-hydroxyphenyl)-2-phenyl-1,2,3,4-tetrahydroquinoline, 3.24 g. sodium methoxide, 150 ml. chlorobenzene and 13 ml. dry methyl alcohol was slowly heated to 100° C. while methyl alcohol was allowed to distill off. N-(2-chloroethyl) diethylamine (8.15 g.) prepared from the corresponding hydrochloride salt by treatment with base was added and the reaction mixture was heated under reflux for three and onehalf hours. The mixture was cooled to 100° C. and a solution of 5 ml. of 35% sodium hydroxide in 100 ml. water was added with vigorous stirring and stirring was continued thirty minutes while the mixture was allowed to cool. The organic phase was separated, the aqueous solution was extracted with chloroform and the combined organic solutions were washed with water and saturated salt solution, dried over sodium sulfate and evaporated to dryness under reduced pressure. The residual material was chromatographed on a column of 500 g. activated magnesium silicate (60–100 mesh) using benzene and benzene containing increasing amounts of ether as eluants and there was thus eluted with 5% ether in benzene 9.4 g. 1-{4-[2-(diethylamino)ethoxy]phenyl}-2-phenyl-1,2,3,4-tetrahydroquinoline.

To a solution of 9.1 g. of the above quinoline in 50 ml. acetone was added a solution of 4.1 g. N-cyclohexanesulfamic acid in 50 ml. acetone and when precipitation began there was added 150 ml. ether. The resulting solid was collected by filtration to give after recrystallization from aceton-ether 11.7 g. of 1-{4-[2-(diethylamino)ethoxy]phenyl}-2-phenyl-1,2,3,4-tetrahydroquinoline cyclohexanesulfamate; m.p. 137° – 138.5° C.

EXAMPLE 2

1-{4-[2-(1-Pyrrolidyl)ethoxy]phenyl}-2-phenyl-1,2,3,4,-tetrahydroquinoline.

A procedure was followed similar to that described in Example 1 but using 19.5 g. 1-(4-hydroxyphenyl)-2-phenyl-1,2,3,4-tetrahydroquinoline, 4.2 g. sodium methoxide, 195 ml. chlorobenzene, 13 ml. dry methyl alcohol and 10.4 g. N-(2-chloroethyl) pyrrolidine. The crude material was chromatographed on 700 g. activated magnesium silicate (60–100 mesh) using benzene and benzene containing increasing amounts of ether as eluants and there was thus eluted with 10% to 50% ether in benzene 10.3 g. 1-{4-[2-(1-pyrrolidyl)ethoxy]phenyl}-2-phenyl-1,2,3,4-tetrahydroquinoline which was converted to the cyclohexanesulfamate salt; m.p. 164°–167° C. (chloroform-ether).

By treating a chilled solution of the free base in ethyl alcohol with ethereal hydrogen chloride until acidic there was obtained 1-{4-[2-(1-pyrrolidyl)ethoxy]phenyl}-2phenyl-1,2,3,4-tetrahydroquinoline hydrochloride; m.p. 187°–189° C.

EXAMPLE 3

1-{4-[2-(Diethylamino)ethoxy]phenyl}-2-(4-chlorophenyl)-1,2,3,4-tetrahydroquinoline.

A procedure was followed similar to that described in Example 1 but using 18 g. 1-(4-hydroxyphenyl)-2-(4-chlorophenyl)-1,2,3,4-tetrahydroquinoline, 3.8 g. sodium methoxide, 160 ml. chlorobenzene, 15 ml. dry methanol and 8.8 g. N-(2-chloroethyl) diethylamine. The crude material was chromatographed on 700 g. activated magnesium silicate (60–100 mesh) using benzene, benzene containing increasing amounts of ether, and ether as eluants and there was thus eluted with 7% – 50% ether in benzene and with ether 15 g. 1-{4-[2-(diethylamino)ethoxy]phenyl}-2-(4-chlorophenyl)-1,2,3,4-tetrahydroquinoline which was converted to the cyclohexanesulfamate salt; m.p. 161°–163° C. (isopropyl alcohol).

EXAMPLE 4

1-{4-[2-(1-Pyrrolidyl)ethoxy]phenyl}-2-(4-chlorophenyl)1,2,3,4-tetrahydroquinoline.

A procedure was followed similar to that described in Example 1 but using 18 g. 1-(4-hydroxyphenyl)-2-(4-chlorophenyl)-1,2,3,4-tetrahydroquinoline, 3.8 g. sodium methoxide, 160 ml. chlorobenzene, 15 ml. dry methyl alcohol and 9 g. N-(2-chloroethyl)pyrrolidine. The crude material was converted to the cyclohexanesulfamate salt and recrystallized successively from isopropyl alcohol and methyl alcohol with charcoal treatment to give 9.5 g. 1-{4-[2-(1-pyrrolidyl)ethoxy]phenyl}-2-(4-chlorophenyl)-1,2,3,4-tetrahydroquinoline cyclohexanesulfamate; m.p. 187°–190° C.

By following a procedure similar to that described in Example 1, but substituting for N-(2-chloroethyl)diethylamine an equivalent amount of the following, ethyl chloride,
n-hexyl chloride,
isopropyl chloride,
N-(3-chloropropyl)diisopropylamine,
N-(2-chloroethyl)morpholine,
N-(2-chloroethyl)thiomorpholine,
N-(2-chloroethyl)piperidine,
N-(2-chloroethyl)piperazine,
N-(2-chloroethyl)-N'-methylpiperazine,
N-(2-chloroethyl)-N'-phenylpiperazine,
N-(2-chloro-1,2,-dimethylethyl)dimethylamine, and
N-(2-chloropropyl)-N-ethyl-N-methylamine, there can be obtained, respectively, 1-(4-ethoxyphenyl)-2-phenyl-1,2,3,4-tetrahydroquinoline,
1-(4-hexoxyphenyl)-2-phenyl-1,2,3,4-tetrahydroquinoline,
1-(4-isopropoxyphenyl)-2-phenyl-1,2,3,4-tetrahydroquinoline,
1-[4-(3-diisopropylaminopropoxy)phenyl]-2-phenyl-1,2,3,4-tetrahydroquinoline,
1-4-[2-(4-morpholinyl)ethoxy]phenyl-2-phenyl-1,2,3,4-tetrahydroquinoline,
1-4-[2-(4-thiomorpholinyl)ethoxy]phenyl-2-phenyl-1,2,3,4-tetrahydroquinoline,
1-4-[2-(1-piperidyl)ethoxy]phenyl-2-phenyl-1,2,3,4-tetrahydroquinoline,
1-4-[2-(1-piperazinyl)ethoxy]phenyl-2-phenyl-1,2,3,4-tetrahydroquinoline,
1-4-[2-(4-methyl-1-piperazinyl)ethoxy]phenyl-2-phenyl-1,2,3,4-tetrahydroquinoline,
1-4-[2-(4-phenyl-1-piperazinyl)ethoxy]phenyl-2-phenyl-1,2,3,4-tetrahydroquinoline,
1-4-[2-(dimethylamino)-1,2-dimethylethoxy]phenyl-2-phenyl-1,2,3,4-tetrahydroquinoline, and
1-4-[2-(N-ethyl-N-methylamino)-1-methylethoxy]phenyl-2-phenyl-1,2,3,4-tetrahydroquinoline.

EXAMPLE 5

1-(4-Hydroxyphenyl)-2-phenyl-1,2,3,4-tetrahydroquinoline.

Procedure I

A solution of 15.5 g. 1-(4-methoxyphenyl)-2-phenyl1,2,3,4-tetrahydroquinoline in 250 ml. glacial acetic acid and 250 ml. hydroqen bromide in acetic acid (48%) was heated under reflux in a nitrogen atmosphere for three hours and then evaporated to dryness under reduced pressure. A suspension of the resulting residue in chloroform was treated with dilute aqueous ammonium hydroxide soln. until basic and the resulting organic soln. was separated, washed with saturated salt solution, dried over sodium sulfate, treated with charcoal and evaporated to dryness under reduced pressure to give 15 g. 1-(4-hydroxyphenyl)-2-phenyl-1,2,3,4-tetrahydroquinoline as a glass.

Procedure 2

Alternatively, 8.5 g. 1-(4-methoxyphenyl)-2-phenyl-1,2,3,4-tetrahydroquinoline, 8.5 g. potassium hydroxide flakes and 85 ml. diethylene glycol were heated to 220° C. for eight hours, poured into 400 ml. ice-water and the organic layer was separated and the aqueous layer was extracted with ether. The organic extracts were combined, washed with water, dilute acetic acid, sodium bicarbonate solution and water, dried over sodium sulfate and evaporated to dryness under reduced pressure. An ethereal solution of the base was treated with ethereal hydrogen chloride to yield 1-(4-hydroxyphenyl)-2-phenyl-1,2,3,4-tetrahydroquinoline hydrochloride; m.p. 189°–192° C.

EXAMPLE 6

1-(4-Hydroxyphenyl)-2-(4-chlorophenyl)-1,2,3,4-tetrahydroquinoline.

Following a procedure similar to that described in Example 5-procedure 1 and using 8 g. 1-(4-methoxyphenyl)-2-(4-chlorophenyl)-1,2,3,4-tetrahydroquinoline in 175 ml. glacial acetic acid and 175 ml. hydrogen bromide in acetic acid (48%) there was obtained a solid which was recrystallized from benzene-hexane to yield 2.7 g. 1-(4-hydroxyphenyl)-2-(4-chlorophenyl)-1,2,3,4-tetrahydroquinoline; m.p. 147°–148.5° C.

EXAMPLE 7

1-(4-Methoxyphenyl)-2-phenyl-1,2,3,4-tetrahydroquinoline

Procedure 1

A solution of 40 g. 3-[2-(4-anisidino)phenyl]-1-phenyl-1-propanol in 1000 ml. xylene and 4.2 g. p-toluenesulfonic acid was heated at reflux for three hours, cooled to room temperature, diluted with 600 ml. ether and washed with sodium bicarbonate solution, water and saturated salt solution. The organic extract was dried and evaporated to dryness under reduced pressure. The residual material was chromatographed on a column of 300 g. activated magnesium silicate (60–100 mesh) using benzene-hexane (1:3) as eluant. The resulting product was crystallized from hexane to yield 8.2 g. 1-(4-methoxyphenyl)-2-phenyl-1,2,3,4-tetrahydroquinoline; m.p. 90.5°–92.5° C.

Procedure 2

To 50 ml. dry tetrahydrofuran cooled to 0° C. were added, with stirring, 1 g. aluminum chloride, stirring and cooling were continued several minutes and 2.5 g. lithium aluminum hydride was added. The stirred mixture was heated at reflux for one-half hour, cooled to 10° C. and a solution of 2.5 g. 1-(4-methoxyphenyl)-2-phenyl-4-(1H)-quinoline in 70 ml. dry tetrahydrofuran was added and stirring was continued at room temperature for sixteen hours. The mixture was cautiously treated with 25 ml. of 10% aqueous sodium hydroxide, filtered and extracted with ether and the ether extract was evaporated to dryness under reduced pressure to give a yellow residue.

The entire procedure was then repeated, substituting the above residue for the quinolone but heating the mixture at reflux for sixteen hours. The resulting yellow oil was chromatographed on a column of 60 g. activated magnesium silicate (60–100 mesh) using benzene with decreasing amounts of hexane as eluant. The material with 1:3 benzenehexane was crystallized from hexane to give 0.9 g. 1-(4-methoxyphenyl)-2-phenyl-1,2,3,4-tetrahydroquinoline; m.p. 91°–93° C.

Procedure 3

To stirred liquid ammonia in a dry atmosphere was added 4 g. potassium metal and a trace of ferric chloride. When the formation of the potassium amide was completed there was added to the stirred mixture 5.8 g. 3-(2-chlorophenyl)-1-phenyl-N-(4-methoxyphenyl)-propylamine and stirring was continued for five hours while the liquid ammonia was allowed to evaporate. The residue was taken up in 200 ml. benzene, and the solution was separated from solids by decantation and evaporated to dryness under reduced pressure. A solution of the residue in chloroform was washed with water, dilute sulfuric acid and water, dried over magnesium sulfate and evaporated to dryness under reduced pressure. The residue was chromatographed on a column of 120 g. activated magnesium silicate using benzene-hexane (1:1) as eluant to give 1-(4-methoxyphenyl)-2-phenyl-1,2,3,4-tetrahydroquinoline; m.p. 88°–90° C.

Procedure 4

3-[2-(4-Anisidino)phenyl]propiophenone (1.67 g.) dissolved in 125 ml. of ethyl alcohol was hydrogenated over 0.5 g. 10% palladium on charcoal initially at a pressure of 37 pounds per square inch and at 60° C. until about an equimolar amount of hydrogen had reacted. The mixture was cooled, filtered, and the filtrate was evaporated to dryness to give an oil which was chromatographed on a column of 100 g. magnesium silicate using benzene-hexane (1:1), benzene and benzene-ether (20:1) as eluants. There was eluted with benzene-hexane (1:1) 0.85 g. of material which on recrystallization from hexane gave 0.40 g. 1-(4-methoxyphenyl)-2-phenyl-1,2,3,4-tetrahydroquinoline; m.p. 91.5°–93.5° C.

In addition, there was eluted with benzene-ether (20:1) 0.5 g. 3-[2-(4-anisidino)phenyl]-1-phenyl-1-propanol.

EXAMPLE 8

1-(4-Methoxyphenyl)-2-(4-chlorophenyl)-1,2,3,4-tetrahydroquinoline

Following a procedure similar to that described in Example 7 (Procedure 1) and using 40 g. 3-[2-(4-anisidino)phenyl]-1-(4-chlorophenyl)-1-propanol in 1000 ml. xylene and 4.2 g. p-toluene sulfonic acid, there was obtained an oily residue which was chromatographed on a column of 700 g. silica gel (100–200 mesh) using hexane and hexane with increasing amounts of benzene as eluants. The material eluted with benzene-hexane (1:1) was recrystallized from hexane to give 6.3 g. 1-(4-methoxyphenyl)-2-(4-chlorophenyl)-1,2,3,4-tetrahydroquinoline; m.p. 97°–100.5° C.

EXAMPLE 9

A. 3-[2-(4-Anisidino)phenyl]-1-phenyl-1-propanol - intermediate for Example 7 - Procedure 1.

A solution of 13.5 g. 3-[2-(4-anisidino)phenyl] propiophenone in 550 ml. ethyl alcohol and 2.5 g. sodium borohydride was stirred at room temperature for three hours and allowed to stand for fifteen hours. The mixture was diluted with 650 ml. water and extracted with ether. The ether extract was washed with water and saturated salt solution, dried and evaporated to dryness. The residue oil was chromatographed on a column of 500 g. magnesium silicate (60–100 mesh) using 1:1 benzene-hexane, benzene and 5% ether in benzene as eluants. There was eluted with 5% ether in benzene 8 g. of material which yielded after recrystallization from benzene-hexane 6.2 g. 3-[2-(4-anisidino)phenyl]-1-phenyl-1-propanol; m.p. 90.5–92° C.

Alternatively, 2.3 g. of 3-[2-(4-anisidino)phenyl]-propiophenone in 100 ml. dry tetrahydrofuran and 2 g. lithium aluminum hydride was stirred and heated under reflux for fourteen hours. The mixture was cooled and 20 ml. of 10% aqueous sodium hydroxide solution was slowly added dropwise and the resulting mixture was filtered. The collected solids were washed with hot chloroform, the combined extracts were evaporated to dryness under reduced pressure and the residue was chromatographed on a column of 100 g. magnesium silicate (60–100 mesh) using benzene and benzene with increasing amounts of ether as eluants. There was thus eluted with ether-benzene (1:20) 1.54 g. material which on recrystallization from benzene-hexane yielded 0.85 g. 3-[2-(4-anisidino)-phenyl]-1-phenyl-1-propanol; m.p. 90.5–92° C.

B. 3-[2-(4-Anisidino)phenyl]propiophenone.

A solution of 27 g. of 1-[4-methoxyphenyl)-3,4-dihydrocarbostyril in 200 ml. benzene and 75 ml. of a 2.1 molar solution of phenyllithium in 75% benzene-ether was heated under reflux in a nitrogen atmosphere for three hours, cooled to room temperature, treated with 200 ml. ice-water and extracted with 200 ml. benzene. The benzene extract was washed with water and saturated salt solution, dried and evaporated to dryness under reduced pressure. The resulting solid residue was recrystallized successively from absolute ethyl alcohol and benzene-hexane to yield 11 g. 3-[2-(4-anisidino)-phenyl]propiophenone; m.p. 110°–112° C.

C. 1-(4-Methoxyphenyl)-3,4-dihydrocarbostyril - intermediate for Example 9B.

A solution of 45 g. 1-(4-methoxyphenyl)carbostyril in 700 ml. absolute alcohol containing one and one-half teaspoons of Raney nickel was hydrogenated at 50° to 60° C. at an initial pressure of about 550 pounds per square inch gauge until approximately the theoretical amount of hydrogen had reacted. The mixture was filtered, the filter pad was washed with ethyl acetate and chloroform, and the combined filtrate was evaporated to dryness under reduced pressure to give after recrystallization from isopropyl alcohol 37.5 g. 1-(4-methoxyphenyl)-3,4-dihydrocarbostyril; m.p. 159°–162° C.

D. 1-(4-Methoxyphenyl)carbostyril 2-(4-Methoxyphenyl)quinoline (104 g.) in 400 ml. mineral oil (extra heavy; sp. gr. 0.880/0.900 at 60° F.) was heated under reflux with stirring in a nitrogen atmosphere for four hours, cooled and diluted with 400 ml. hexane. The resulting crystals were collected by filtration and recrystallized from benzene to give 48 g. 1-(4-methoxyphenyl)carbostyril; m.p. 158°–160° C.

E. 2-(4-Methoxyphenoxy)quinoline.

To a stirred suspension of 32 g. sodium hydride (52% suspension in mineral oil) in 475 ml. dimethylformamide and 475 ml. 1,2-dimethoxyethane was added, portionwise during about fifteen minutes, 59.5 g. 4-methoxphenyl followed by, after five minutes, a solution of 95.5 g. 2-chloroquinoline in 130 ml. dimethyl formamide in one portion and the resulting mixture was heated under reflux for sixteen hours, cooled to 5° C., poured into 4000 ml. ice-water and extracted with ether. The ether extract was washed with ice cold 2% aqueous sodium hydroxide solution, water and saturated salt solution, dried and evaporated to dryness under reduced pressure. The resulting crystals were recrystallized from benzene-hexane to give 104 g. 2-(4-methoxyphenyl)-quinoline; m.p. 96.5°–98° C.

EXAMPLE 10

A. 3-[2-(4-Anisidino)phenyl]-1-(4-chlorophenyl)-1-propanol - intermediate for Example 8

Following a procedure similar to that described in Example 9A and using 59 g. 3-[2-(4-anisidino)phenyl]-4'-chloropropiophenone, 1200 ml. ethyl alcohol and 15 g. sodium borohydride there was obtained, after evaporation to dryness of the ether extract, 66 g. 3[2-(4-anisidino)phenyl]-1-(4-chlorophenyl)-1-propanol as an amber oil which was used in the next step without further purification.

B. 3-[2-(4-Anisidino)phenyl -4'-chloropropiophenone.

A solution of 67.5 g. 4-chlorobromobenzene in 350 ml. dry ether was added dropwise with stirring and in a nitrogen atmosphere to 193 ml. of a solution (1.6 molar) of butyllithium in hexane during twenty-five minutes and stirring was continued ten minutes to give a solution of 4-chlorophenyllithium.

Following a procedure similar to that described in Example 9B and using 42 g. 1-(4-methoxyphenyl)-3,4-dihydrocarbostyril in 600 ml. benzene and the 4-chlorophenyllithium solution above there was obtained 59 g. 3-[2-(4-anisidino)phenyl]phenyl]-4'-chloropropiophenone as a light brown semi-solid oil which was used in the next step without further purification.

EXAMPLE 11

A. 1-{4-[2-(Diethylamino)ethoxy]phenyl}-6-methoxy-3,4dihydrocarbostyril

A mixture of 6.5 g. 6-methoxy-3,4-dihydrocarbostyril, 10 g. 2-(4-bromophenoxy)triethylamine, 3.7 g. potassium carbonate and 1 g. copper powder were heated in an oil bath, the temperature of which was held at 252° C., for eighteen hours. The mixture was cooled to room temperature and treated with 50 ml. ethyl acetate and the copper and potassium carbonate were removed by filtration. The filtrate was evaporated to dryness and the residue was treated with diluted aqueous hydrochloric acid solution and the resulting solution was washed with ether, made basic (pH 10) and extracted with ether. The ether extract was with water and saturated salt solution, dried and evaporated to dryness. The residue was chromatographed on a column of 200 g. magnesium silicate (60–100 mesh) using benzene with increasing amounts of ether, ether, 5% methyl alcohol in ether, and ether with increasing amounts of triethylamine (1% and 3%) as eluants. The material eluted with 1% triethylamine in ether was crystallized from hexane to give 1.7 g. of 1-{4-[2-(diethylamino)ethoxy]phenyl}-6-methoxy-3,4-dihydrocarbostyril; m.p. 97.5°–100° C.

B. 2-(4-Bromophenoxy)triethylamine

To a stirred mixture of sodium 4-bromophenoxide in chlorobenzene, prepared by mixing 86.5 g. 4-bromophenol with 32.4 g. sodium methoxide in 1500 ml. chlorobenzene and 130 ml. absolute methyl alcohol, heating the resulting mixture slowly to 120° C. while allowing methyl alcohol to distill off, and subsequent cooling to 100° C., was added 81.5 g. 2-diethylaminoethyl chloride in one portion and the resulting solution was heated under reflux for three and one-half hours. The mixture was cooled to 110° C., a solution of 50 ml. 35% sodium hydroxide in 1000 ml. water was added, and cooling was continued to room temperature with vigorous stirring. The separated aqueous phase was extracted with chloroform, the extract was combined with the organic phase and the combined organic solutions were washed with water, saturated salt solution, dried and evaporated to dryness to give after distillation under reduced pressure 109 g. 2-(4-bromophenoxy)triethylamine; b.p. 95°–97° C. (0.1–0.15 mm); $N^{25}D1.5305$.

C. 6-Methoxy-3,4-dihydrocarbostyril

To a solution, prepared by mixing 8.2 g. 6-hydroxy-3,4-dihydrocarbostyril with 50 ml. water containing 2 g. sodium hydroxide, was added dropwise with stirring 8.5 ml. dimethyl sulfate (sp. gr. 1.332). During the course of the addition the resulting mixture was maintained at about pH 10 by periodic additions of 10% sodium hydroxide solution. The mixture was stirred for two and one-half hours at room temperature, filtered and the collected solids were washed thoroughly with water to give after recrystallization from methyl alcohol 6.3 g. 6-methoxy-3,4-dihydrocarboxtyril; m.p. 142.5°–143.5° C.

D. 6-Hydroxy-3,4-dihydrocarbostyril

A mixture of 3-chloropropionanisidide and 135 g. aluminum chloride were slowly heated, with vigorous stirring, to the melting point of the anisidide. The resulting liquid was then heated at 150° C. for one-half hour and poured hot onto cracked ice containing hydrochloric acid. The resulting solid was collected by filtration, washed with water and recrystallized from methyl alcohol to give 28 g. 6-hydroxy-3,4-dihydrocarbostyril; m.p. 238°–240° C.

E. 3-Chloropropionanisidide

To a stirred solution of 195 g. 4-anisidine in 350 ml. dry acetone was added dropwise a solution of 100 g. 3-chloropropionyl chloride in 350 ml. dry acetone causing gentle reflux and heating under reflux was continued for one hour after addition was completed. The mixture was poured into 3000 ml. water containing 30 ml. concentrated hydrochloric acid. The resulting solid was collected by filtration, washed with water, and recrystallized from methyl alcohol to give 85 g. 3-chloropropionanisidide; m.p. 120.5°–122.5° C.

By following a procedure similar to that described in Example 9B and substituting for 1-(4-methoxyphenyl)-3,4-dihydrocarbostyril an equivalent amount of 1-{4-[2-(diethylamino)ethoxy]phenyl}-6-methoxy-3,4-dihydrocarboxtyril there can be obtained 3-<2-{4-[2-(diethylamino)ethoxy]anilino}-5-methoxyphenyl>propiophenone.

By following a procedure similar to that described in Example 9A and substituting for 3-[2-(4-anisidino)phenyl]propiophenone an equivalent amount of 3-<2-{4-[2-(diethylamino)ethoxy]anilino}-5-methoxyphenyl>propiophenone there can be obtained 3-<2-{4-[2-(diethylamino)ethoxy]anilino}-5-methoxyphenyl>-1-phenyl-1-propanol.

By following a procedure similar to that described in Example 7 (Procedure 1) and substituting for 3-[2-(4-anisidino)phenyl]-1-phenyl-1-propanol an equivalent amount of 3-<2-{4-[2-(diethylamino)ethoxy]anilino}-5-methoxyphenyl>-1-phenyl-1-propanol there can be obtained 1-{4-[2-(diethylamino)ethoxy]phenyl}-2-phenyl-6-methoxy-1,2,3,4-tetrahydroquinoline.

EXAMPLE 12

1-(4-Methoxyphenyl)-2-phenyl-4(1H)-quinolone - intermediate for Example 7 (Procedure 2) and Example 18B.

Procedure I

2-Acetylphenyl N-(4-methoxyphenyl)benzimidate (100 g.) was slowly heated to 250° C. in a nitrogen atmosphere with stirring. The temperature of the exothermic reaction which rose quickly to 320° C., was allowed to come to 250° C., and heating was continued for one-half hour. The reaction mixture was cooled and the residue recrystallized from absolute ethyl alcohol to give 71 g. 1-(4-methoxyphenyl)-2-phenyl-4(1H)-quinolone; m.p. 202°–204° C.

Procedure 2

1-(4-Methoxyphenyl)-2-phenyl-4(1H)quinolone-3-carboxylic acid (1.2 g.) was heated in an oil bath at 280° C. until gas evolution ceased. The residue was crystallized from ethyl alcohol to give 0.8 g. 1-(4-methoxyphenyl)-2-phenyl-4(1H)-quinolone; m.p. 197°–198° C.

Procedure 3

To a solution of 2-(methylsulfinyl)-2'-(4-methoxyanilino)acetophenone (0.3 g.) in 3 ml. benzene was added 0.1 ml. of benzaldehyde and 1 drop of pyridine and the solution was heated under reflux for three hours. The resulting mixture was concentrated under reduced pressure and then one-half of the residue was recrystallized from ethyl alcohol to give 0.18 g. 1-(4-methoxyphenyl)-2-phenyl-4(1H)-quinolone; m.p. 200°–201° C.

Following a procedure similar to that described in Example 12, Procedure 3, but substituting for benzaldehyde an equivalent amount of 4-bromobenzaldehyde, 4-fluorobenzaldehyde, 4-iodobenzaldehyde, 4-methylbenzaldehyde, 4-isopropylbenzaldehyde, 4-butylbenzaldehyde, 4-methoxybenzaldehyde, 4-isopropoxybenzaldehyde, and 4-hexoxybenzaldehyde there can be obtained, respectively, 1-(4-methoxyphenyl)-2-(4-bromophenyl)-4(1H)-quinolone, 1-(4-methoxyphenyl)-2-(4-fluorophenyl)-4(1H)-quinolone, 1-(4-methoxyphenyl)-2-(4-iodophenyl)-4(1H)-quinolone, 1-(4-methoxyphenyl)-2-(4-methylphenyl)-4(1H)-quinolone, 1-(4-methoxyphenyl)-2-(4-isopropylphenyl)-4(1H)- quinolone, 1-(4-methoxyphenyl)-2-(4-butylphenyl)-4(1H)-quinolone, 1-(4-methoxyphenyl)-2-(4-methoxyphenyl)-4(1H)-quinolone, 1-(4-methoxyphenyl)-2-(4-isopropoxyphenyl)-4(1H)-quinolone, and 1-(4-methoxyphenyl)-2-(4-hexoxyphenyl)-4(1H)-quinolone.

Following a procedure similar to that described in Example 7, Procedure 2, but substituting for 1-(4-methoxyphenyl)-2-phenyl-4(1H)-quinolone an equivalent amount of the quinolones listed in the previous paragraph there can be obtained, respectively, 1-(4-methoxyphenyl)-2-(4-bromophenyl)-1,2,3,4-tetrahydroquinoline, 1-(4-methoxyphenyl)-2-(4-fluorophenyl)-1,2,3,4-tetrahydroquinoline, 1-(4-methoxyphenyl)-2-(4-iodophenyl)-1,2,3,4-tetrahydroquinoline, 1-(4-methoxyphenyl)-2-(4-methylphenyl)-1,2,3,4-tetrahydroquinoline, 1-(4-methoxyphenyl)-2-(4-isopropylphenyl)-1,2,3,4-tetrahydroquinoline, 1-(4-methoxyphenyl)-2-(4-butylphenyl)-1,2,3,4-tetrahydroquinoline, 1-(4-methoxyphenyl)-2-(4-methoxyphenyl)-1,2,3,4-tetrahydroquinoline, 1-(4-methoxyphenyl)-2-(4-isopropoxyphenyl)-1,2,3,4-tetrahydroquinoline, and 1-(4-methoxyphenyl)-2-(4-hexoxyphenyl)-1,2,3,4-tetrahydroquinoline.

Following a procedure similar to that described in Example 5, but substituting for 1-(4-methoxyphenyl)-2-phenyl-1,2,3,4-tetrahydroquinoline an equivalent amount of the tetrahydroquinolines listed in the previous paragraph, excluding 1-(4-methoxyphenyl)-2-(4-methoxyphenyl)-1,2,3,4-tetrahydroquinoline, there can be obtained, respectively, 1-(4-hydroxyphenyl)-2-(4-bromophenyl)-1,2,3,4-tetrahydroquinoline, 1-(4-hydroxyphenyl)-2-(4-fluorophenyl)-1,2,3,4-tetrahydroquinoline, 1-(4-hydroxyphenyl)-2-(4-iodophenyl)-1,2,3,4-tetrahydroquinoline, 1-(4-hydroxyphenyl)-2-(4-methylphenyl)-1,2,3,4-tetrahydroquinoline, 1-(4-hydroxyphenyl)-2-(4-isopropylphenyl)-1,2,3,4-tetrahydroquinoline, 1-(4-hydroxyphenyl)-2-(4-butylphenyl)-1,2,3,4-tetrahydroquinoline, 1-(4-hydroxyphenyl)-2-(4-isopropoxyphenyl)-1,2,3,4-tetrahydroquinoline, and 1-(4-hydroxyphenyl)-2-(4-hexoxyphenyl)-1,2,3,4-tetrahydroquinoline.

Following a procedure similar to that described in Example 1, but substituting for 1-(4-hydroxyphenyl)-2-phenyl-1,2,3,4-tetrahydroquinoline and equivalent amount of the quinolines listed in the previous paragraph there can be obtained, respectively, 1-{4-[2-(diethylamino)ethoxy]phenyl}-2-(4-bromophenyl)-1,2,3,4-tetrahydroquinoline, 1-{4-[2-(diethylamino)ethoxy]phenyl}-2-(4-fluorophenyl)-1,2,3,4-tetrahydroquinoline, 1-{4-[2-(diethylamino)ethoxy]phenyl}-2-(4-iodophenyl)-1,2,3,4-tetrahydroquinoline, 1-{4-[2-(diethylamino)ethoxy]phenyl}-2-(4-methylphenyl)-1,2,3,4-tetrahydroquinoline, 1-{4-[2-(diethylamino)ethoxy]phenyl}-2-(4-isopropylphenyl)-1,2,3,4-tetrahydroquinoline, 1-{4-[2-(diethylamino)ethoxy]phenyl}-2-(4-butylphenyl)-1,2,3,4-tetrahydroquinoline, 1-{4-[2-(diethylamino)ethoxy]phenyl}-2-(4-isopropoxyphenyl)-1,2,3,4-tetrahydroquinoline, and 1-{4-[2-(diethylamino)ethoxy]phenyl}-2-(4-hexoxyphenyl)-1,2,3,4-tetrahydroquinoline.

EXAMPLE 13

A. 2-Acetylphenyl N-(4-Methoxyphenyl)benzimidate - intermediate for Example 12 (Procedure 1)

To a stirred solution of 59 g. sodium methoxide in 1100 ml. dry methyl alcohol was added 148 g. 2'-hydroxyacetophenone while the temperature was maintained at 20° C. After several minutes stirring there was added a solution of 225 g. N-(4-methoxyphenyl)benzimidoyl chloride in 460 ml. ethyl acetate and stirring at room temperature was continued for fifteen hours. The organic solvent was evaporated under reduced pressure, the residue was dissolved in ethyl acetate and the resulting solution was washed with water, saturated salt solution, dried, and evaporated to dryness to give after recrystallization from ethyl alcohol 203 g. 2-acetylphenyl N-(4-methoxyphenyl)benzimidate; m.p. 127°–129° C.

B. N-(4-Methoxyphenyl)benzimidoyl Chloride

A mixture of 284 g. 4-methoxybenanilide and 260 g. phosphorus pentachloride was slowly heated to reflux with stirring and heating under reflux was continued for two hours. The mixture was distilled under reduced pressure to give 225 g. N-(4-methoxyphenyl)benzimidoyl chloride; b.p. 125°–130° C. (0.05 mm.).

C. 4-Methoxybenzanilide

To a stirred solution of 187.5 g. 4-anisidine in 2000 ml. ethylene dichloride and 217.5 ml. triethylamine was added a solution of 175.5 ml. benzoyl chloride in 25 ml. ethylene dichloride dropwise while the temperature was maintained at 10° to 20° C. The resulting precipitate was collected by filtration, washed with water and recrystallized from absolute ethyl alcohol to give 259 g. 4-methoxybenzanilide; m.p. 156°–158° C.

Following a procedure similar to that described in Example 13A, but substituting for 2'-hydroxyacetophenone an equivalent amount of 5'-bromo-2'-hydroxyacetophenone, 5'-chloro-2'-hydroxyacetophenone, 5'-fluoro-2'-hydroxyacetophenone, 5'-ethoxy-2'-hydroxyacetophenone, 5'-methyl-2'-hydroxyacetophenone, 5'-pentyl-2'-hydroxyacetophenone, and 5'-isopropyl-2'-hydroxyacetophenone, there can be obtained, respectively, 2-acetyl-4-bromophenyl N-(4-methoxyphenyl)benzimidate, 2-acetyl-4-chlorophenyl N-(4-methoxyphenyl)benzimidate, 2-acetyl-4-fluorophenyl N-(4-methoxyphenyl)benzimidate, 2-acetyl-4-ethoxyphenyl N-(4-methoxyphenyl)benzimidate, 2-acetyl-4-methylphenyl N-(4-methoxyphenyl)benzimidate, 2-acetyl-4-pentylphenyl N-(4-methoxyphenyl)benzimidate, and 2-acetyl-4-isopropylphenyl N-(4-methoxyphenyl)benzimidate.

Following a procedure similar to Example 12, Procedure 1, but substituting for 2-acetylphenyl N-(4-methoxyphenyl)benzimidate an equivalent amount of the benzimidates listed in the previous paragraph there can be obtained, respectively, 1-(4-methoxyphenyl)-2-phenyl-6-bromo-4(1H)-quinolone, 1-(4-methoxyphenyl)-2-phenyl-6-chloro-4(1H)-quinolone, 1-(4-methoxyphenyl)-2-phenyl-6-fluoro-4(1H)-quinolone, 1-(4-methoxyphenyl)-2-phenyl-6-ethoxy-4(1H)-quinolone, 1-(4-methoxyphenyl)-2-phenyl-6-methyl-4(1H)-quinolone, 1-(4-methoxyphenyl)-2-phenyl-6-pentyl-4(1H)-quinolone, and 1-(4-methoxyphenyl)-2-phenyl-6-isopropyl-4(1H)-quinolone.

Following a procedure similar to that described in Example 7, Procedure 2, but substituting for 1-(4-methoxy)-2-phenyl-4(1H)-quinolone an equivalent amount of the quinolones listed in the previous paragraph there can be obtained respectively, 1-(4-methoxyphenyl)-2-phenyl-6-bromo-1,2,3,4-tetrahydroquinolone, 1-(4-methoxyphenyl)-2-phenyl-6-chloro-1,2,3,4-tetrahydroquinoline, 1-(4-methoxyphenyl)-2-phenyl-6-fluoro-1,2,3,4-tetrahydroquinoline, 1-(4-methoxyphenyl)-2-phenyl-6-ethoxy-1,2,3,4-tetrahydroquinoline, 1-(4-methoxyphenyl)-2-phenyl-6-methyl-1,2,3,4-tetrahydroquinoline, 1-(4-methoxyphenyl)-2-phenyl-6-pentyl-1,2,3,4-tetrahydroquinoline, and 1-(4-methoxyphenyl)-2-phenyl-6-isopropyl-1,2,3,4-tetrahydroquinoline.

Following a procedure similar to that described in Example 5, but substituting for 1-(4-methoxyphenyl)-2-phenyl-1,2,3,4-tetrahydroquinoline an equivalent amount of the quinolines listed in the previous paragraph there can be obtained, respectively, 1-(4-hydroxyphenyl)-2-phenyl-6-bromo-1,2,3,4-tetrahydroquinoline, 1-(4-hydroxyphenyl)-2-phenyl-6-chloro-1,2,3,4-tetrahydroquinoline, 1-(4-hydroxyphenyl)-2-phenyl-6-fluoro-1,2,3,4-tetrahydroquinoline, 1-(4-hydroxyphenyl)-2-phenyl-6-ethoxy-1,2,3,4-tetrahydroquinoline, 1-(4-hydroxyphenyl)-2-phenyl-6-methyl-1,2,3,4-tetrahydroquinoline, 1-(4-hydroxyphenyl)-2-phenyl-6-pentyl-1,2,3,4-tetrahydroquinoline, and 1-(4-hydroxyphenyl)-2-phenyl-6-isopropyl-1,2,3,4-tetrahydroquinoline.

Following a procedure similar to that described in Example 3, but substituting for 1-(4-hydroxyphenyl)-2-(4-chlorophenyl)-1,2,3,4-tetrahydroquinoline an equivalent amount of the quinolines listed in the previous paragraph there can be obtained, respectively, 1-{4-[2-(diethylamino)ethoxy]phenyl}-2-phenyl-6-bromo-1,2,3,4-tetrahydroquinoline, 1-{4-[2-(diethylamino)ethoxy]phenyl}-2-phenyl-6-chloro-1,2,3,4-tetrahydroquinoline, 1-{4-[2-(diethylamino)ethoxy]phenhy}-2-phenyl-6-fluoro-1,2,3,4-tetrahydroquinoline, 1-{4-[2-(diethylamino)-ethoxy]phenyl}-2-phenyl-6-ethoxy-1,2,3,4-tetrahydroquinoline, 1-{4-[2-(diethylamino)ethoxy]phenyl}-2-phenyl-6-methyl-1,2,3,4-tetrahydroquinoline, 1-{4-[2-(diethylamino)ethoxy]phenyl}-2-phenyl-6-pentyl-1,2,3,4-tetrahydroquinoline, and 1-{4-[2-(diethylamino)-ethoxy]phenyl}-2-phenyl-6-isopropyl-1,2,3,4-tetrahydroquinoline.

EXAMPLE 14

A.

1-(4-Methoxyphenyl)-2-phenyl-4(1H)-quinolone-3-carboxylic Acid - intermediate for Example 12 (Procedure 2)

A solution of 25 g. ethyl -(4-methoxyphenyl)-2-phenyl-4(1H)-quinolone-3-carboxylate in 300 ml. ethyl alcohol and 30 ml. 35% aqueous sodium hydroxide solution was heated under reflux for twenty minutes. The solution was concentrated under reduced pressure and the resulting solid was dissolved in 400 ml. water and the solution was acidified with hydrochloric acid. The resulting solid was collected by filtration, redissolved in sodium hydroxide solution and precipitated by addition of hydrochloric acid. The resulting solid was collected by filtration and dissolved in 300 ml. chloroform and the solution was treated with charcoal and evaporated to dryness to give after crystallization from cyclohexane 12.1 g. 1-(4-methoxyphenyl)-2-phenyl-4(1H)-quinolone-3-carboxylic acid; m.p. 263° C. (dec.).

B. Ethyl 1-(4-Methoxyphenyl)-2-phenyl-4(1H)-quinolone-3-carboxylate

Sodium hydride (5 g.; 50% in mineral oil) was dissolved in 60 ml. dimethyl sulfoxide at 65° to 75° C. in a nitrogen atmosphere during two hours. To this solution at 15° C. and with cooling was added 17.3 ml. ethyl benzoylacetate during three minutes followed by a solution of N-(4-methoxyphenyl)-isatoic anhydride in 50 ml. dimethyl sulfoxide. The temperature of the reaction was raised to 50° C. whereuopn gas evolution began. When gas evolution ceased the temperature was raised to 70° C. and the mixture was stirred for one hour and then allowed to stand at room temperature for fifteen hours. The resulting precipitate was collected by filtration and recrystallized from benzene-cyclohexane to give 18.2 g. ethyl 1-(4-methoxyphenyl)-2-phenyl-4(1H)-quinolone-3-carboxylate; m.p. 246°-247° C.

C. N-(4-Methoxyphenyl)isatoic Anhydride

N-(4-Methoxyphenyl)anthranilic acid (35.5 g.) and 170 ml. ethyl chloroformate were heated under reflux for fifteen hours. The solvent was evaporated under reduced pressure and the solid was triturated with ether, collected by filtration, washed with ether and recrystallized from tetrahydrofuran to give 22 g. of N-(4-methoxyphenyl)isatoic anhydride; m.p. 215°-216° C.

D. N-(4-Methoxyphenyl)anthranilic Acid

A mixture of 80 g. 2-chlorobenzoic acid, 80 g. 4-anisidine, 80 g. potassium carbonate, 4 g. activated copper powder, and 800 ml. amyl alcohol was heated under reflux with efficient stirring for four hours. The amyl alcohol was removed by steam distillation and the remaning aqueous phase was filtered and made neutral by addition of 1:1 concentrated hydrochloric acid-water. The resulting solid (102 g.) was collected by filtration to give after recrystallization from isopropyl alcohol N-(4-methoxyphenyl)anthranilic acid; m.p. 183°-184° C.

EXAMPLE 15

2-Methylsulfinyl)-2'-(4-methoxyanilino)acetophenone - intermediate for Example 12 (Procedure 3)

To a 2 molar solution of dimsyl sodium in dimethylsulfoxide (365 ml.), cooled to 10° C., was added a solution of 65 g. of N-(4-methoxyphenyl)isatoic anhydride in 150 ml. dimethylsulfoxide with stirring and stirring was continued 30 minutes at room temperature and one hour at 50° C. The reaction mixture was poured onto 1200 g. of ice, 70 ml. of concentrated hydrochloric acid was added, and the mixture was extracted with methylene dichloride. The extract was washed with water, dried (MgSO₄), and concentrated under reduced pressure to give, after recrystallization from benzene-cyclohexane 45 g. 2-(methylsulfinyl)-2'-(4-methoxyanilino)acetophenone; m.p. 115°-116° C.

EXAMPLE 16

A.

2-(Methylsulfinyl)-2'-(4-benzyloxanilino)-5'-methoxyacetophenone

Following the procedure given in Example 15 and using 135 ml. of a 2 molar solution of dimsyl sodium in dimethylsulfoxide, 30 g. of N-(4-benzyloxyphenyl)-5-methoxyisatoic anhydride in 100 ml. of dimethylsulfoxide, 700 g. of ice and 20 ml. of concentrated hydrochloric acid there was obtained after recrystallization from benzene-hexane 19 g. 2-(methylsulfinyl)-2'-(4-benzyloxyanilino)-5'-methoxyacetophenone; m.p. 128°-129° C.

B. N-(4-Benzyloxyphenyl)-5-methoxyisatoic Anhydride

Following a procedure similar to that described in Example 14C and using 65 g. N-(4-benzyloxyphenyl)-5-methoxyanthranilic acid and 270 ml. ethyl chloroformate there was obtained 46 g. N-(4-benzyloxyphenyl)-5-methoxyisatoic anhydride; m.p. 206°–207° C.

C. N-(4-Benzyloxyphenyl)-5-methoxyanthranilic Acid

Following a procedure similar to that described in Example 14D and using 101 g. 2-bromo-5-methoxybenzoic acid, 131 g. 4-benzyloxyaniline, 70 g. potassium carbonate, 5 g. activated copper powder and 160 ml. amyl alcohol there was obtained after successive recrystallizations from isopropyl alcohol and benzene-cyclohexane 68 g. of N-(4-benzyloxyphenyl)-5-methoxyanthranilic acid; m.p. 167°–168° C.

D. 2-Bromo-5-methoxybenzoic Acid

To a solution of 100 g. 3-methoxybenzoic acid in 400 ml. glacial acetic acid was added in one portion a solution of 34 ml. bromine (sp. gr. 3.12) in 200 ml. glacial acetic acid followed by 400 ml. water. The solution was heated to the boiling point and then cooled to 5° C. and the precipitate was collected by filtration and washed with water to give 110 g. of 2-bromo-5-methoxybenzoic acid; m.p. 154°–157° C.

Following a procedure similar to that described in Example 12, Procedure 3, but substituting for 2-(methylsulfinyl)-2'-(4-methoxyanilino)acetophenone an equivalent amount of 2-(methylsulfinyl)-2'-(4-benzyloxyanilino)-5'-methoxyacetophenone there can be obtained 1-(4-benzyloxyphenyl)-2-phenyl-6-methoxy-4(1H)-quinolone.

Following a procedure similar to that described in Example 7, Procedure 2, but substituting for 1-(4-methoxyphenyl)-2-phenyl-4(1H)-quinolone an equivalent amount of 1-(4-benzyloxyphenyl)-2-phenyl-6-methoxy-4(1H)-quinolone there can be obtained 1-(4-hydroxyphenyl)-2-phenyl-6-methoxy-1,2,3,4-tetrahydroquinoline.

Following a procedure similar to that described in Example 1, but substituting for 1-(4-hydroxyphenyl)-2-phenyl-1,2,3,4-tetrahydroquinoline an equivalent amount of 1-(4-hydroxyphenyl)-2-phenyl-6-methoxy-1,2,3,4-tetrahydroquinoline there can be obtained 1-{4-[2-(diethylamino)ethoxy]-phenyl}-2-phenyl-6-methoxy-1,2,3,4-tetrahydroquinoline and corresponding cyclohexanesulfamate salt.

EXAMPLE 17

A. 3-(2-Chlorophenyl)-1-phenyl-N-(4-methoxyphenyl)-propylamine - intermediate for Example 7 (Procedure 3)

To a stirred suspension of 1.5 g. lithium aluminum hydride in 50 ml. dry tetrahydrofuran was added a solution of 2.6 g. N-[3-(2-chlorophenyl)-1-phenyl-1-propylidene]-4-anisidine in 15 ml. dry tetrahydrofuran and the mixture was heated under reflux for two hours, cooled and then treated with 3 ml. water in 10 ml. tetrahydrofuran. The hot mixture was filtered and the filtrate was evaporated to dryness under reduced pressure to give after successive recrystallizations from benzene and isopropyl alcohol 0.85 g. 3-(2-chlorophenyl)-1-phenyl-N-(4-methoxyphenyl)propylamine; m.p. 214°–215° C.

B. N-[3-(2-Chlorophenyl)-1-phenyl-1-propylidene]-4-anisidine 3-(2-Chlorophenyl)-1-phenyl-1-propanone (12.24 g.), 6.15 g. 4-anisidine and 1.2 g. 4-anisidine-zinc chloride in xylene were heated under reflux for six hours, water being removed by means of a water separating apparatus (Dean Stark). The reaction mixture was filtered and the filrate was concentrated under reduced pressure. The residual oil was distilled under reduced pressure and the fraction distilling at 185°–189° C. (0.1 mm.) solidified on standing and was recrystallized from hexane to give 3.65 g. of N-[3-(2-chlorophenyl)-1-phenyl-1-propylidene]-4-anisidine; m.p. 83.5°–84.5° C.

C. 3-(2-Chlorophenyl)-1-phenyl-1-propanone

A solution of 97 g. 2-chlorochalcone in 800 ml. absolute alcohol containing 5 g. of Raney nickel was subjected to a hydrogen atmosphere for one and one-half hours at an initial pressure of 165 lbs./sq. inch gauge. The reaction mixture was filtered and the filtrate was evaporated to dryness under reduced pressure. The residue was crystallized from hexane to give 73.5 g. 3-(2-chlorophenyl)-1-phenyl-1-propanone; m.p. 44°–45° C.

D. 2-Chlorochalcone

To 230 ml. 2-chlorobenzaldehyde and 234 ml. acetophenone in 400 ml. absolute ethyl alcohol was added a solution of 17 ml. aqueous 35% sodium hydroxide in 52 ml. water with stirring and stirring was continued for one hour. The reaction mixture was made neutral by addition of a solution of 12 ml. concentrated hydrochloric acid in 120 ml. water, cooled and the resulting precipitate was filtered to give after recrystallization from methyl alcohol 306 g. 2-chlorochalcone; m.p. 51°–52° C.

Following a procedure similar to that described in Example 17D but substituting for 2-chlorobenzaldehyde equivalent amounts of 2-chloro-5-methoxybenzaldehyde and in each case for acetophenone an equivalent amount of 4'-bromoacetophenone, 4'-pentoxyacetophenone, 4'-isopentoxyacetophenone and 4'-methoxyacetophenone there can be obtained, respectively, 2-chloro-5-methoxy-4'-bromochalcone, 2-chloro-5-methoxy-4'-pentoxychalcone, 2-chloro-5-methoxy-4'-isopentoxychalcone, and 2-chloro-5-methoxy-4'-methoxychalcone.

Following a procedure similar to that described in Example 17C but substituting for 2-chlorochalcone an equivalent amount of the chalcones listed in the previous paragraph there can be obtained, respectively, 3-(2-chloro-5-methoxyphenyl)-1-(4-bromophenyl)-1-propanone, 3-(2-chloro-5-methoxyphenyl)-1-(4-pentoxyphenyl)-1-propanone, 3-(2-chloro-5-methoxyphenyl)-1-(4-isopentoxyphenyl)-1-propanone, and 3-(2-chloro-5-methoxyphenyl)-1-(4-methoxyphenyl)-1-propanone.

Following a procedure similar to that described in Example 17B but substituting for 3-(2-chlorophenyl)-1-phenyl-1-propanone an equivalent amount of the propanones listed in the previous paragraph and in each case for 4-anisidine an equivalent amount of 4-benzyloxyaniline there can be obtained, respectively, N-[3-(2-chloro-5-methoxyphenyl)-1-(4-bromophenyl)-1-propylidene]-4-benzyloxyaniline, N-[3-(2-chloro-5-methoxyphenyl)-

1-(4-pentoxyphenyl)-1-propylidene]-4-benzyloxyaniline, N-[3-(2-chloro-5-methoxyphenyl)-1-(4-isopentoxyphenyl)-1-propylidene]-4-benzyloxyaniline, and N-[3-(2-chloro-5-methoxyphenyl)-1-(4-methoxyphenyl)-1-propylidene]-4-benzyloxyaniline.

Following a procedure similar to that described in Example 17A but substituting for N-[3-(2-chlorophenyl)-1-phenyl-1-propylidene]-4-anisidine an equivalent amount of the anilines listed in the previous paragraph there can be obtained, respectively, 3-(2-chloro-5-methoxyphenyl)-1-(4-bromophenyl)-N-(4-benzyloxyphenyl)propylamine, 3-(2-chloro-5-methoxyphenyl)-1-(4-pentoxyphenyl)-N-(4-benzyloxyphenyl)propylamine, 3-(2-chloro-5-methoxyphenyl)-1-(4-isopentoxyphenyl)-N-(4-benzyloxyphenyl)propylamine, and 3-(2-chloro-5-methoxyphenyl)-1-(4-methoxyphenyl)-N-(4-benzyloxyphenyl)propylamine.

Following a procedure similar to that described in Example 7, Procedure 3, but substituting for 3-(2-chlorophenyl)-1-phenyl-N-(4-methoxyphenyl)propylamine an equivalent amount of the propylamines listed in the previous paragraph there can be obtained, respectively, 1-(4-benzyloxyphenyl)-2-(4-bromophenyl)-6-methoxy-1,2,3,4-tetrahydroquinoline, 1-(4-benzyloxyphenyl)-2-(4-pentoxyphenyl)-6-methoxy-1,2,3,4-tetrahydroquinoline, 1-(4-benzyloxyphenyl)-2-(4-isopentoxyphenyl)-6-methoxy-1,2,3,4-tetrahydroquinoline, and 1-(4-benzyloxyphenyl)-2-(4-methoxyphenyl)-6-methoxy-1,2,3,4-tetrahydroquinoline.

Following the standard debenzylation procedure described hereinbefore in Method B there can be obtained from the 1,2,3,4-tetrahydroquinolines listed in the previous paragraph, respectively, 1-(4-hydroxyphenyl)-2-(4-bromophenyl)-6-methoxy-1,2,3,4-tetrahydroquinoline, 1-(4-hydroxyphenyl)-2-(4-pentoxyphenyl)-6-methoxy-1,2,3,4-tetrahydroquinoline, 1-(4-hydroxyphenyl)-2-(4-isopentoxyphenyl)-6-methoxy-1,2,3,4-tetrahydroquinoline, and 1-(4-hydroxyphenyl)-2-(4-methoxyphenyl)-6-methoxy-1,2,3,4-tetrahydroquinoline.

Following a procedure similar to that described in Example 2 but substituting for 1-(4-hydroxyphenyl)-2-phenyl-1,2,3,4-tetrahydroquinoline an equivalent amount of the 1,2,3,4-tetrahydroquinolines listed in the previous paragraph there can be obtained, respectively, 1-{4-[2-(1-pyrrolidyl)ethoxy]phenyl}-2-(4-bromophenyl)-6-methoxy-1,2,3,4-tetrahydroquinoline, 1-{4-[2-(1-pyrrolidyl)ethoxy]phenyl}-2-(4-pentoxyphenyl)-6-methoxy-1,2,3,4-tetrahydroquinoline, 1-{4-[2-(1-pyrrolidyl)-ethoxy]phenyl}-2-(4-isopentoxyphenyl)-6-methoxy-1,2,3,4-tetrahydroquinoline, and 1-{4-[2-(1-pyrrolidyl)ethoxy]phenyl}-2-(4-methoxyphenyl)-6-methoxy-1,2,3,4-tetrahydroquinoline.

EXAMPLE 18

A.
1-{4-[2-(Diethylamino)ethoxy]phenyl}-2-phenyl-4(1H)-quinolone

By following a procedure similar to that described in Example 1 and using 49.5 g. 1-(4-hydroxyphenyl)-2-phenyl-4(1H)-quinolone, 10.5 g. sodium methoxide, 500 ml. chlorobenzene, 45 ml. dry methyl alcohol, and 26 g. N-(2-chloroethyl)diethylamine in 80 ml. chlorobenzene there was obtained on evaporation to dryness of the chloroform extract and recrystallization from isopropyl alcohol 32 g. 1-{4-[2-(diethylamino)ethoxy]phenyl}-2-phenyl-4(1H)-quinolone; m.p. 115°–117° C.

B. 1-(4-Hydroxyphenyl)-2-phenyl-4(1H)-quinolone

Following a procedure similar to that described in Example 5 (Procedure 1) and using 16 g. 1-(4-methoxyphenyl)-2-phenyl-4(1H)-quinolone, 250 ml. glacial acetic acid and 250 ml. hydrogen bromide in acetic acid (48%) there was obtained after recrystallization from dimethylformamide-methyl alcohol 1-(4-hydroxyphenyl)-2-phenyl-4(1H)-quinolone; m.p. 374°–377° C.

By following a procedure similar to that described in Example 7 (Procedure 2) and substituting for 1-(4-methoxyphenyl)-2-phenyl-4(1H)-quinolone an equivalent amount of 1-{4-[2-(diethylamino)ethoxy]phenyl}-2-phenyl-4(1H)-quinolone there can be obtained 1-{4-[2-(diethylamino)ethoxy]phenyl}-2-phenyl-1,2,3,4-tetrahydroquinoline.

EXAMPLE 19

A. 1-(4-Benzyloxyphenyl)-3,4-dihydrocarbostyril

To a solution of 7.9 g. of 1-(4-hydroxyphenyl)-3,4-dihydrocarbostyril in 70 ml. of absolute ethyl alcohol was added 15 g. of potassium carbonate and 4.6 ml. of benzyl chloride, and the mixture was heated under reflux for three hours. The mixture was filtered hot, cooled, and the resulting solid was filtered to give 8.1 g. of 1-(4-benzyloxyphenyl)-3,4-dihydrocarbostyril, m.p. 145° C. (methyl alcohol).

B. 1-(4-Hydroxyphenyl)-3,4-dihydrocarbostyril

A solution of 25.33 g. of 1-(4-methoxyphenyl)-3,4-dihydrocarbostyril in 200 ml. of a 48% solution of hydrogen bromide in acetic acid was heated under reflux for fifteen hours. The mixture was cooled, filtered, and the solid was washed with water to give 22.1 g. of 1-(4-hydroxyphenyl)-3,4-dihydrocarbostyril, m.p. 240°–241° C.

Following a procedure similar to that described in Example 9B but substituting for 1-(4-methoxyphenyl)-3,4-dihydrocarbostyril an equivalent amount of 1-(4-benzyloxyphenyl)-3,4-dihydrocarbostyril and in each case for phenyllithium an equivalent amount of 4-methoxyphenyllithium, 4-ethoxyphenyllithium, and 4-fluorophenyllithium there can be obtained, respectively, 3-[2-(4-benzyloxyanilino)phenyl]-4'-methoxypropiophenone, 3-[2-(4-benzyloxyanilino)phenyl]-4'-ethoxypropiophenone, and 3-[2-(4-benzyloxyanilino)phenyl]-4'-fluoropropiophenone.

Following a procedure similar to that described in Example 9A but substituting for 3-[2-(4-anisidino)phenyl]propiophenone an equivalent amount of the propiophenones listed in the previous paragraph there can be obtained, respectively, 3-[2-(4-benzyloxyanilino)phenyl]-1-(4-methoxyphenyl)-1-propanol, 3-[2-(4-benzyloxyanilino)phenyl]-1-(4-ethoxyphenyl)-1-propanol, and 3-[2-(4-benzyloxyanilino)phenyl]-1-(4-fluorophenyl)-1-propanol.

Following a procedure similar to that described in Example 7, Procedure 1, but substituting for 3-[2-(4-anisidino)phenyl]-1-phenyl-1-propanol an equivalent amount of the propanols listed in the previous paragraph there can be obtained, respectively, 1-(4-benzyloxyphenyl)-2-(4-methoxyphenyl)-1,2,3,4-tetrahydroquinoline, 1-(4-benzyloxyphenyl)-2-(4-ethoxyphenyl)-1,2,3,4-tetrahydroquinoline, and 1-(4-benzyloxyphenyl)-2-(4-fluorophenyl)-1,2,3,4-tetrahydroquinoline.

Following the standard debenzylation procedure described hereinbefore in Method B, there can be obtained from the tetrahydroquinolines listed in the previous paragraph, respectively, 1-(4-hydroxyphenyl)-2-(4-methoxyphenyl)-1,2,3,4-tetrahydroquinoline, 1-(4-hydroxyphenyl)-2-(4-ethoxyphenyl)-1,2,3,4-tetrahydroquinoline, and 1-(4-hydroxyphenyl)-2-(4-fluorophenyl)-1,2,3,4-tetrahydroquinoline.

Following a procedure similar to that described in Example 2 but substituting for 1-(4-hydroxyphenyl)-2-phenyl-1,2,3,4-tetrahydroquinoline an equivalent amount of the quinolines listed in the previous paragraph there can be obtained, respectively, 1-{4-[2-(1-pyrrolidyl)ethoxy]phenyl}-2-(4-methoxyphenyl)-1,2,3,4-tetrahydroquinoline, 1-{4-[2-(1-pyrrolidyl)ethoxy]phenyl}-2-(4-ethoxyphenyl)-1,2,3,4-tetrahydroquinoline, and 1-{4-[2-(1-pyrrolidyl)ethoxy]phenyl}-2-(4-fluorophenyl)-1,2,3,4-tetrahydroquinoline.

I claim:
1. A compound of the formula

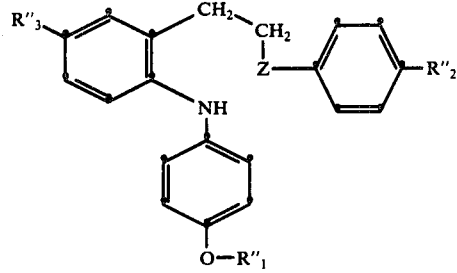

where $R''_1$ is lower-alkyl or benzyl;
$R''_2$ is hydrogen, lower-alkoxy or halo;
$R''_3$ is hydrogen or lower-alkoxy;
and Z is carbonyl or hydroxymethylene.

2. A compound according to claim 1 where $R''_1$ is lower-alkyl.

3. A compound according to claim 2 where $R''_2$ is hydrogen or halo, and $R''_3$ is hydrogen.

4. 3-[2-(4-Anisidino)phenyl]-1-phenyl-1-propanol according to claim 3.

5. 3-[2-(4-Anisidino)phenyl]-1-(4-chlorophenyl)-1-propanol according to claim 3.

6. 3-[2-(4-Anisidino)phenyl]propiophenone according to claim 3.

7. 3-[2-(4-Anisidino)-phenyl]-4'-chloropropiophenone according to claim 3.